United States Patent
Williams

(10) Patent No.: US 11,399,838 B2
(45) Date of Patent: Aug. 2, 2022

(54) RELOAD ASSEMBLY FOR CIRCULAR STAPLING DEVICES

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 107 days.

(21) Appl. No.: 16/829,027

(22) Filed: Mar. 25, 2020

(65) Prior Publication Data
US 2020/0330099 A1 Oct. 22, 2020

Related U.S. Application Data

(60) Provisional application No. 62/836,889, filed on Apr. 22, 2019.

(51) Int. Cl.
*A61B 17/072* (2006.01)
*A61B 17/115* (2006.01)
*A61B 17/00* (2006.01)

(52) U.S. Cl.
CPC ... *A61B 17/1155* (2013.01); *A61B 2017/0053* (2013.01); *A61B 2017/00486* (2013.01); *A61B 2017/07257* (2013.01); *A61B 2017/07271* (2013.01); *A61B 2017/07285* (2013.01)

(58) Field of Classification Search
CPC ...... A61B 2017/07285; A61B 17/1155; A61B 17/068; A61B 17/072; A61B 2017/07271
USPC .................................................. 227/180.1
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Sep. 18, 2020, corresponding to counterpart European Application No. 20170560.5; 8 pages.

*Primary Examiner* — Gloria R Weeks
(74) *Attorney, Agent, or Firm* — Carter, DeLuca & Farrell LLP

(57) ABSTRACT

A reload assembly includes a shell housing, and a staple cartridge supported on a distal portion of the shell housing. The reload assembly further includes a pusher, a knife carrier supported, and a holder, each of which is supported within the annular cavity. The pusher is movable from a retracted position, through a partially advanced position, to a fully advanced position. The knife carrier includes at least one flexible arm having a free end. The at least one flexible arm has a hook portion on the free end. A housing of the holder defines at least one opening for receiving the hook portion of the at least one flexible arm of the knife carrier which is received within the at least one opening of the holder when the pusher is in the retracted position and is deflected from within the at least one opening when the pusher is in the partially advanced position.

19 Claims, 9 Drawing Sheets

(56) References Cited

U.S. PATENT DOCUMENTS

| | | | |
|---|---|---|---|
| 4,207,898 A | 6/1980 | Becht | |
| 4,289,133 A * | 9/1981 | Rothfuss | A61B 17/115 227/175.3 |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A * | 3/1986 | Conta | A61B 17/115 227/179.1 |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A * | 10/1988 | Green | A61B 17/115 227/19 |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A * | 9/1990 | Lipatov | A61B 17/115 227/180.1 |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A * | 12/1993 | Grant | A61B 17/115 227/179.1 |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A * | 12/1996 | Schnut | A61B 17/115 227/175.1 |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 * | 2/2001 | Bittner | A61B 17/1114 227/180.1 |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |

(56) References Cited

U.S. PATENT DOCUMENTS

| | | |
|---|---|---|
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 * | 1/2007 | Milliman ............ A61B 17/1114 227/175.1 |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 * | 4/2008 | Milliman ............ A61B 17/068 227/175.1 |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 * | 8/2010 | Chen .................... A61B 17/115 227/180.1 |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |

(56) References Cited

U.S. PATENT DOCUMENTS

| | | |
|---|---|---|
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,573,464 B2 * | 11/2013 | Nalagatla ............ A61B 17/1155 227/179.1 |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,421,013 B2 * | 8/2016 | Patel .................... A61B 17/068 |
| 10,405,864 B2 * | 9/2019 | Zhan .................. A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0278346 A1 * | 11/2011 | Hull .................... A61B 17/1155 227/180.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0292368 A1 * | 11/2012 | Nalagatla ............ H04B 7/0682 227/175.2 |
| 2012/0325888 A1 | 12/2012 | Qiao et al. |

(56) References Cited

U.S. PATENT DOCUMENTS

| | | |
|---|---|---|
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0014393 A1* | 1/2015 | Milliman ............... A61B 90/98 227/176.1 |
| 2015/0048140 A1* | 2/2015 | Penna ................... A61B 90/98 227/176.1 |
| 2015/0108201 A1* | 4/2015 | Williams ............... A61B 90/98 227/177.1 |
| 2015/0173757 A1* | 6/2015 | Williams ............. A61B 17/072 227/180.1 |
| 2015/0201930 A1* | 7/2015 | Aranyi ............. A61B 17/07207 227/177.1 |
| 2016/0000428 A1* | 1/2016 | Scirica ............... A61B 1/00089 227/180.1 |
| 2016/0007999 A1* | 1/2016 | Latimer ............... A61B 17/105 227/177.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0249929 A1* | 9/2016 | Cappola ................. A61B 90/98 227/176.1 |
| 2016/0302792 A1 | 10/2016 | Motai |
| 2018/0233850 A1* | 8/2018 | Penna ................. A61B 17/1155 |
| 2020/0138441 A1* | 5/2020 | Sgroi, Jr. ........... A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2823774 A2 | 1/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

RELOAD ASSEMBLY FOR CIRCULAR STAPLING DEVICES

CROSS-REFERENCE TO RELATED APPLICATIONS

This application claims the benefit of and priority to U.S. Provisional Patent Application Ser. No. 62/836,889 filed Apr. 22, 2019, the entire disclosure of which is incorporated by reference herein

BACKGROUND

1. Technical Description

The present disclosure is directed to circular stapling devices and, more particularly, to reload assemblies for circular stapling devices with structure to retain a knife carrier in a retracted position prior to and after firing of the stapling device.

2. BACKGROUND OF RELATED ART

Conventional circular stapling devices include an elongate body and a shell or reload assembly supported on a distal portion of the elongate body. The reload assembly includes a shell housing, a staple cartridge supported on the shell housing having a plurality of staples, a pusher assembly, a knife defining a cylindrical cavity, and a knife carrier that supports the knife and is movable through the staple cartridge to core tissue. The pusher assembly includes an annular pusher and a staple pushing member that is engaged with the annular pusher and is movable to move the staple pushing member to eject staples from the staple cartridge.

After a stapling device has been operated to staple and cut tissue, the knife carrier and the knife are retracted to withdraw the knife into the shell housing. This serves two purposes. The first is to move the knife to a position to allow removal of a tissue donut from within the cavity defined by the knife. The second is to position the knife in a location recessed within the shell housing to avoid injury to a clinician during manipulation and disposal of the reload assembly.

A continuing need exists in the art for a reload assembly that includes improved structure for retaining the knife/knife carrier in a retracted position.

SUMMARY

A reload assembly according to the present disclosure includes a shell housing, and a staple cartridge supported on a distal portion of the shell housing. The shell housing includes an inner housing portion and an outer housing portion. The inner housing portion spaced from the outer housing portion to define an annular cavity. The staple cartridge having a plurality of staple pockets. Each of the staple pockets receive a staple. The reload assembly further includes a pusher supported within the annular cavity, a knife carrier supported within the annular cavity and defining a longitudinal axis, and a holder including a housing. The pusher is movable from a retracted position, through a partially advanced position to a fully advanced position. The knife carrier includes at least one flexible arm having a free end. The at least one flexible arm has a hook portion on the free end. The housing of the holder defines a cavity configured to releasably receive a chip, and at least one opening for receiving the hook portion of the at least one flexible arm of the knife carrier. The hook portion of the at least one flexible arm is received within the at least one opening of the holder when the pusher is in the retracted position and is deflected from within the at least one opening when the pusher is in the partially advanced position.

In embodiments, the pusher includes an inner tapered surface, and the at least one flexible arm includes a ramp portion. The inner tapered surface of the pusher may engage the ramp portion of the knife carrier when the pusher is in the partially advanced position. When the pusher is in the retracted position, the hook portion of the at least one flexible arm may be received within the at least one opening of the holder.

The reload assembly may further include a bushing secured to the inner housing portion. The holder may be secured to the bushing. The housing of the reload may include an annular flange portion receivable about the bushing. The at least one flexible arm may include two flexible arms. The hook portion may include an angled surface that engages the holder as the knife carrier moves from an advanced position to a retracted position. The knife carrier may be moveable from a retracted position to an advanced position when the hook portion of the at least one flexible arm is spaced from the at least one opening in the holder. The knife carrier may be secured to the holder when the hook portion of the at least one flexible arm is received within the at least one opening.

In some embodiments, the pusher includes an annular pusher and a pushing member. The pushing member may include fingers that are received within the staple pockets of the staple cartridge.

The reload assembly may further include an annular knife secured to the knife carrier. The chip may be an e-prom chip.

A surgical device includes a handle assembly, and a reload assembly releasably securable to the handle assembly. The reload assembly includes a shell housing, and a staple cartridge supported on a distal portion of the shell housing. The reload assembly further includes a pusher supported within the shell housing, a knife carrier defining a longitudinal axis and supporting a knife, and a holder including a housing. The pusher is movable from a retracted position, through a partially advanced position to a fully advanced position. The knife carrier includes at least one flexible arm having a free end. The at least one flexible arm has a hook portion on the free end. The housing of the holder defines a cavity configured to releasably receive a chip, and at least one opening for receiving the hook portion of the at least one flexible arm of the knife carrier. The hook portion of the at least one flexible arm is received within the at least one opening of the holder when the pusher is in the retracted position and is deflected from within the at least one opening when the pusher is in the partially advanced position.

In embodiments, the pusher includes an inner tapered surface, and the at least one flexible arm includes a ramp portion. The inner tapered surface of the pusher may engage the ramp portion of the knife carrier when the pusher is in the partially advanced position. When the pusher is in the retracted position, the hook portion of the at least one flexible arm may be received within the at least one opening of the holder.

The reload assembly may further include a bushing secured to the inner housing portion. The holder may be secured to the bushing. The housing of the reload may include an annular flange portion receivable about the bushing. The at least one flexible arm may include two flexible arms. The hook portion may include an angled surface that engages the holder as the knife carrier moves from an advanced position to a retracted position. The knife carrier may be moveable from a retracted position to an advanced position when the hook portion of the at least one flexible arm is spaced from the at least one opening in the holder. The knife carrier may be secured to the holder when the hook portion of the at least one flexible arm is received within the at least one opening.

In some embodiments, the pusher includes an annular pusher and a pushing member. The pushing member may include fingers that are received within the staple pockets of the staple cartridge.

The reload assembly may further include an annular knife secured to the knife carrier. The chip may be an e-prom chip.

BRIEF DESCRIPTION OF THE DRAWINGS

Various embodiments of the presently disclosed reload assembly are described herein below with reference to the drawings, wherein.

DETAILED DESCRIPTION OF EMBODIMENTS

Figures 1, 2:
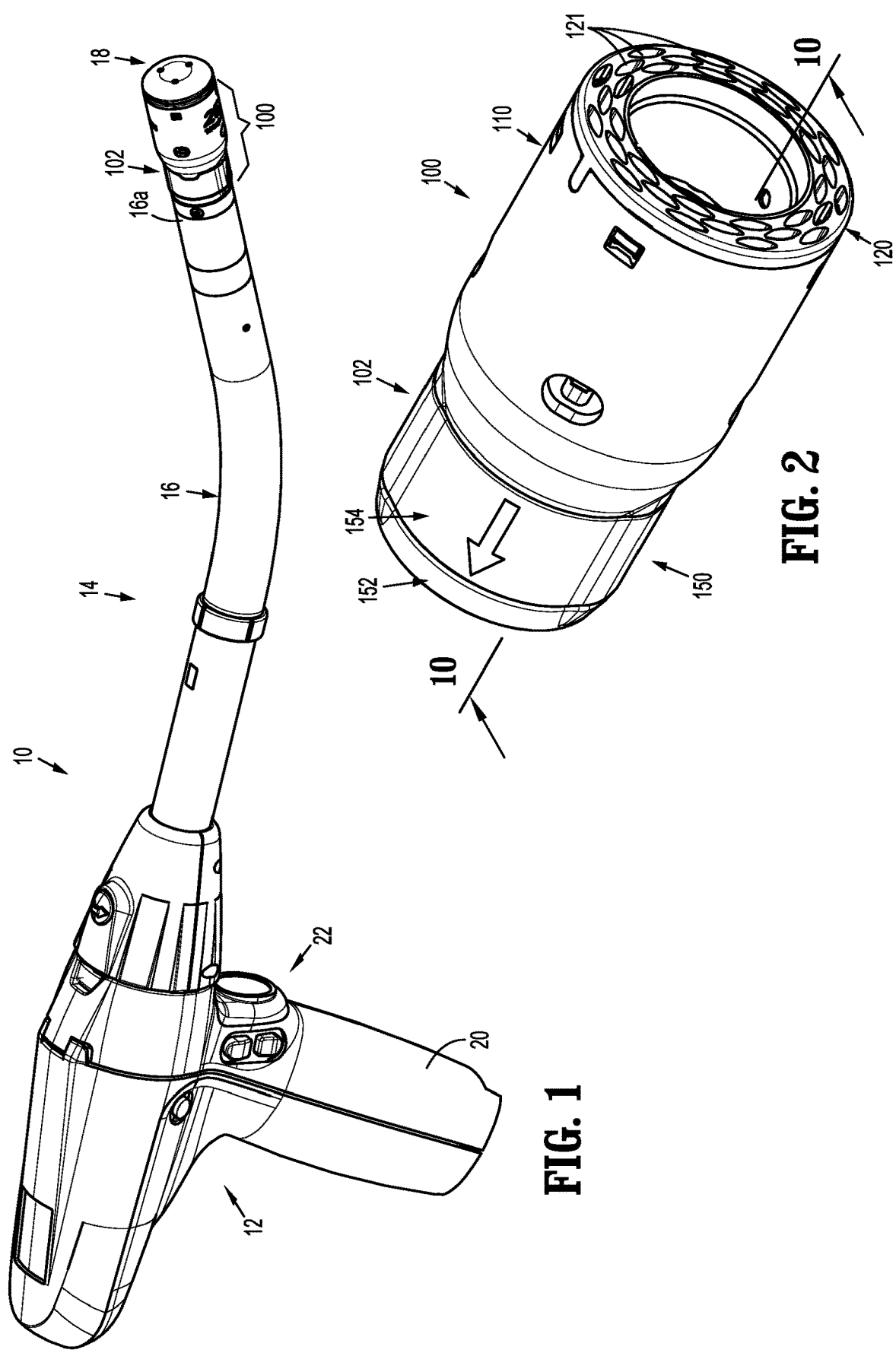
FIG. 1 is a side perspective view of a circular stapling device including an exemplary embodiment of the presently disclosed reload assembly in accordance with the present disclosure.
FIG. 2 is a side perspective view of the reload assembly of FIG. 1.

The presently disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

FIGS. 1 and 2 illustrate a circular stapling device 10 including an exemplary embodiment of the presently disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. The reload assembly 100 includes a proximal portion 102 that is releasably coupled to a distal portion 16a of the elongate body 16. The handle assembly 12 includes a stationary grip 20 that supports actuation buttons 22 for controlling operation of various functions of the stapling device 10 including approximation of the reload and anvil assemblies 100, 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. No. 9,055,943 (the '943 Patent), U.S. Pat. No. 9,023,014 (the '014 Patent), and U.S. Publication Nos. 2018/0125495, and 2017/0340351 which are incorporated herein by reference in their entirety.

Figure 3:
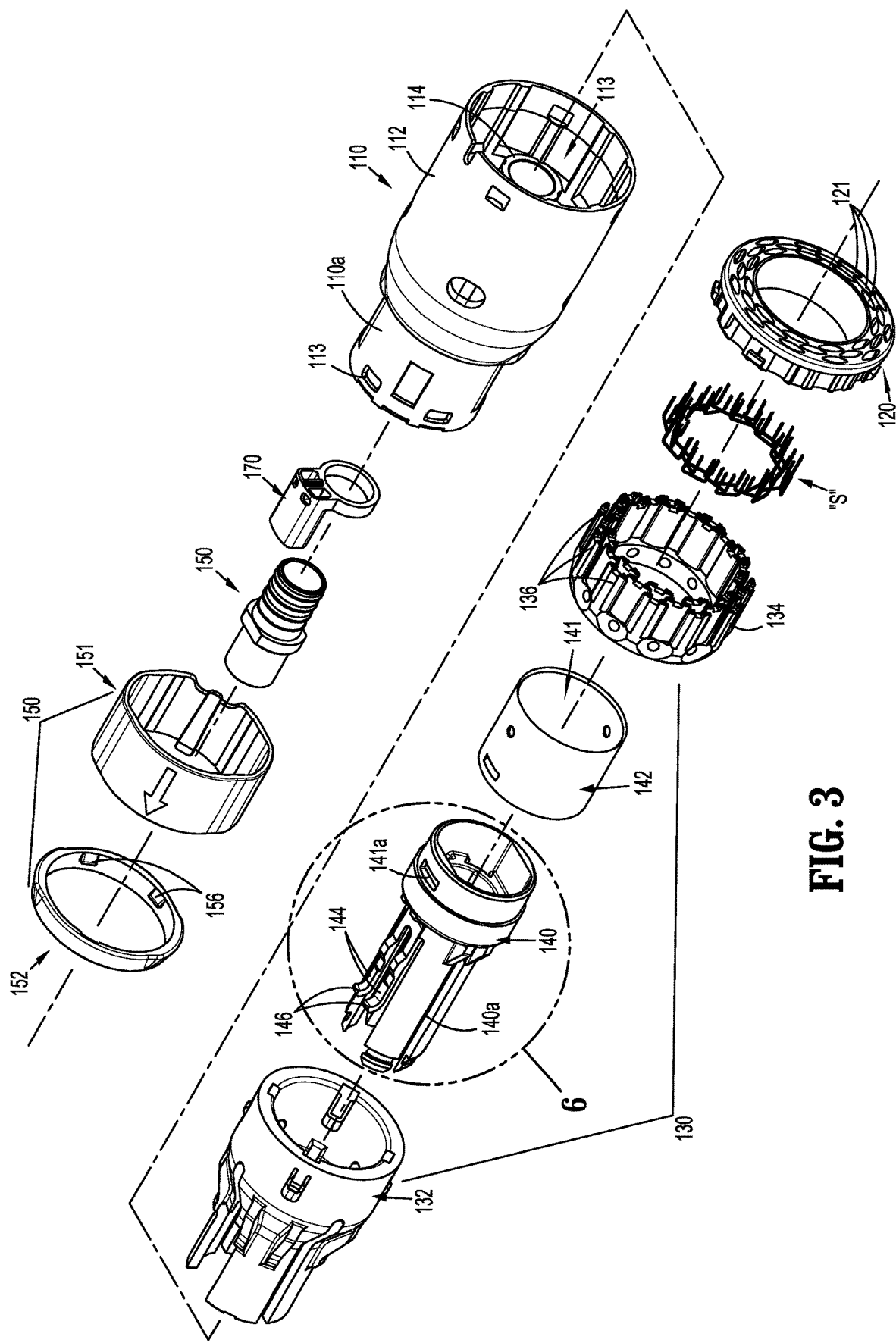
FIG. 3 is an exploded side perspective view of the reload assembly of FIG. 2.

Referring to FIGS. 2 and 3, the reload assembly 100 includes a shell housing 110, a staple cartridge 120 supporting a plurality of staples "S", a staple pusher assembly 130, and a knife carrier 140 supporting an annular knife 132. The staple cartridge 120 is annular and defines annular rows of staple pockets 121. Each of the staple pockets 121 supports one of the plurality of staples "S" (FIG. 3).

Figure 4:
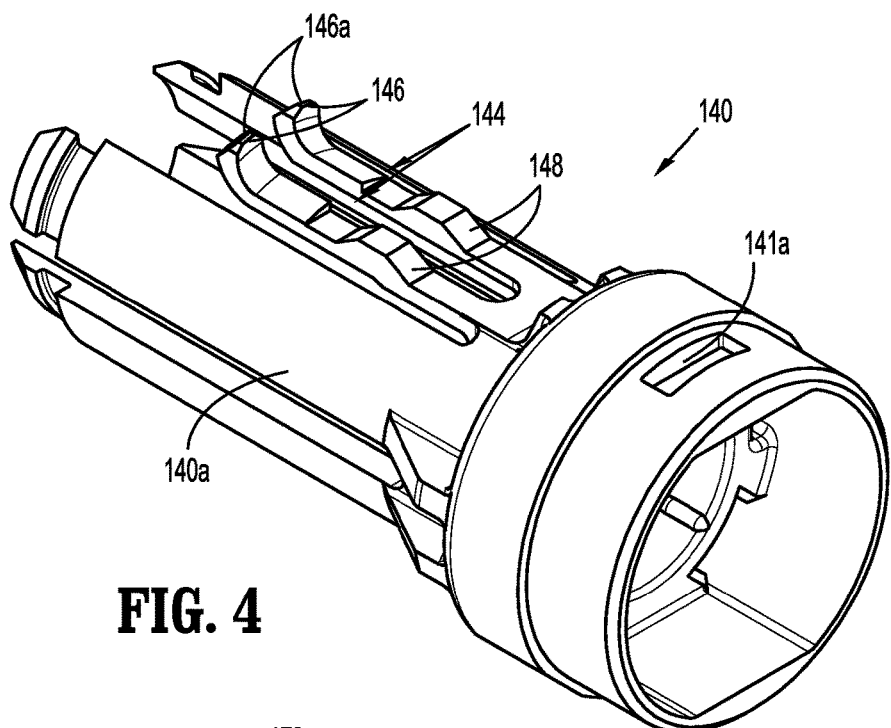
FIG. 4 is a perspective view of a knife carrier of the reload assembly of FIG. 2.

The pusher assembly 130 of the reload assembly 100 includes a staple pushing member 132 and an annular pusher 134 that together define a longitudinal through bore 131 (FIG. 4). The annular pusher 134 has a distal portion that abuts a proximal portion of the staple pushing member 132 such that distal movement of the annular pusher 134 within the shell housing 110 causes distal movement of the staple pushing member 132 within the shell housing 110. The staple pushing member 132 of the reload assembly 100 has a plurality of fingers 136. Each of the plurality of fingers 136 is received within a respective one of the staple pockets 121 of the staple cartridge 120 and is movable through the respective staple pocket 121 to eject the staples "S" from the staple pockets 121 when the staple pushing member 132 is moved from a retracted position to an advanced position within the shell housing 110.

Figure 14:
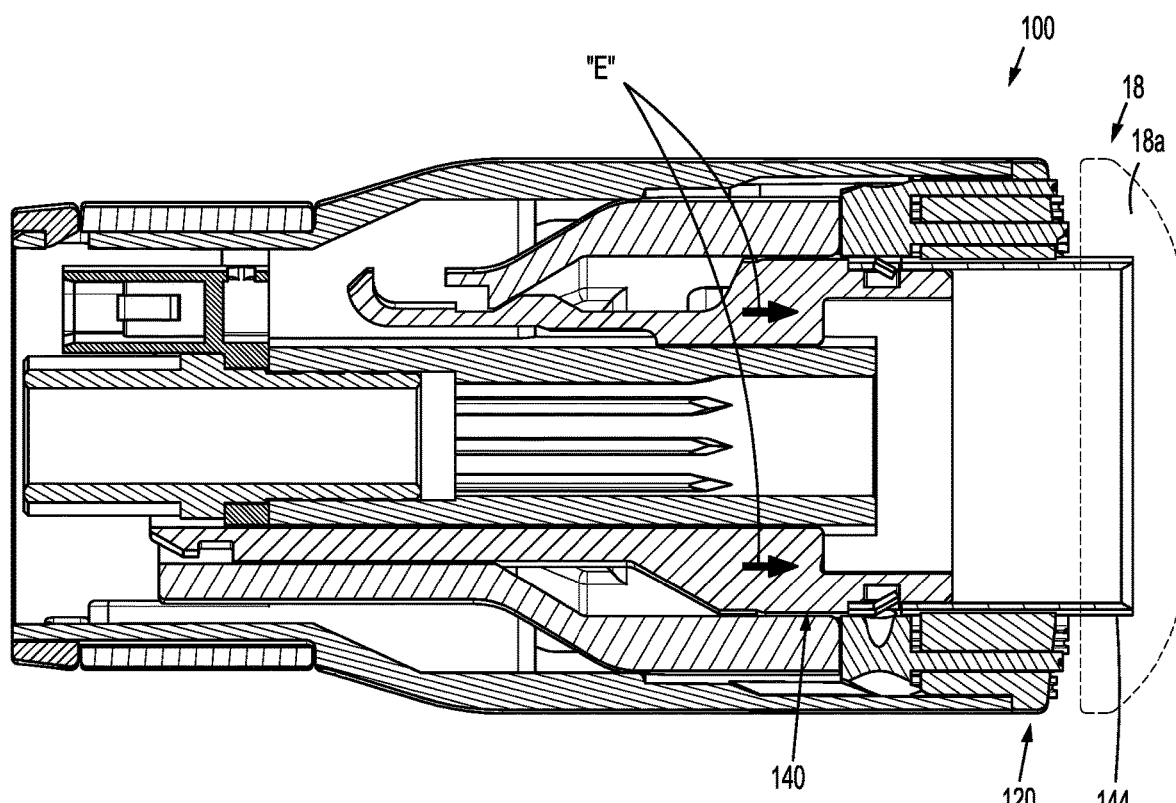
FIG. 14 is a cross-sectional view as shown in FIG. 10 with the knife carrier in a fully advanced position.

The shell housing 110 of the reload assembly 100 includes an outer housing portion 112 and an inner housing portion 114 spaced from the outer housing portion 112 to define an annular cavity 113. The pusher assembly 130 and the knife carrier 140, including the annular knife 142, are movable within the annular cavity 113 between retracted (FIG. 10) and advanced positions (FIG. 14). The pusher assembly 130 is movable from its retracted position to its advanced position (FIG. 11) independently of the knife carrier 140 to eject the staples "S" from the staple cartridge 120.

The annular knife 142 is supported about an outer surface of the knife carrier 140 and defines a cylindrical cavity 141. In embodiments, the annular knife 142 includes projections 142a (FIG. 10) that are received in openings 141a on the knife carrier 140 to secure the annular knife 142 about the knife carrier 140. Alternately, other fastening techniques may be used to secure the knife 142 to the knife carrier 140.

With additional reference to FIG. 4, the knife carrier 140 includes a pair of flexible arms 144 that extend along a proximal section 140a of the knife carrier 140. The ends of the flexible arms 144 include a hook portion 146. As will be described in further detail below, the hook portions 146 are configured to selectively engage an e-prom holder 170 of the reload assembly 100 to prevent premature advancement of the knife carrier 140 and to retain the knife carrier 140 in a retracted position subsequent to firing. Although shown including a pair of flexible arms 144, it is envisioned that the knife carrier 140 may include only one arm, or may including more than two arms.

With continued reference to FIGS. 2 and 3, the shell housing 110 includes a proximal portion 110a that supports a coupling mechanism 150 that is operable to couple the reload assembly 100 to the adaptor assembly 14 (FIG. 1) of the stapling device 10. The coupling mechanism 150 includes a retaining member 152 and a coupling member 154. The coupling member 154 is received about the proximal portion 110a of the shell housing 110 and is configured to engage a distal end of the adaptor assembly 14 to couple the reload assembly 100 to the adaptor assembly 14. In embodiments, the retaining member 152 includes projections 156 that are received in openings 113 (FIG. 3) in the proximal portion 110a of the shell housing 110 to secure the retaining member 152 and the coupling member 154 to the shell housing 110. It is envisioned that other coupling mechanisms can be used to secure the reload assembly 100 to the adaptor 14.

Figure 5:
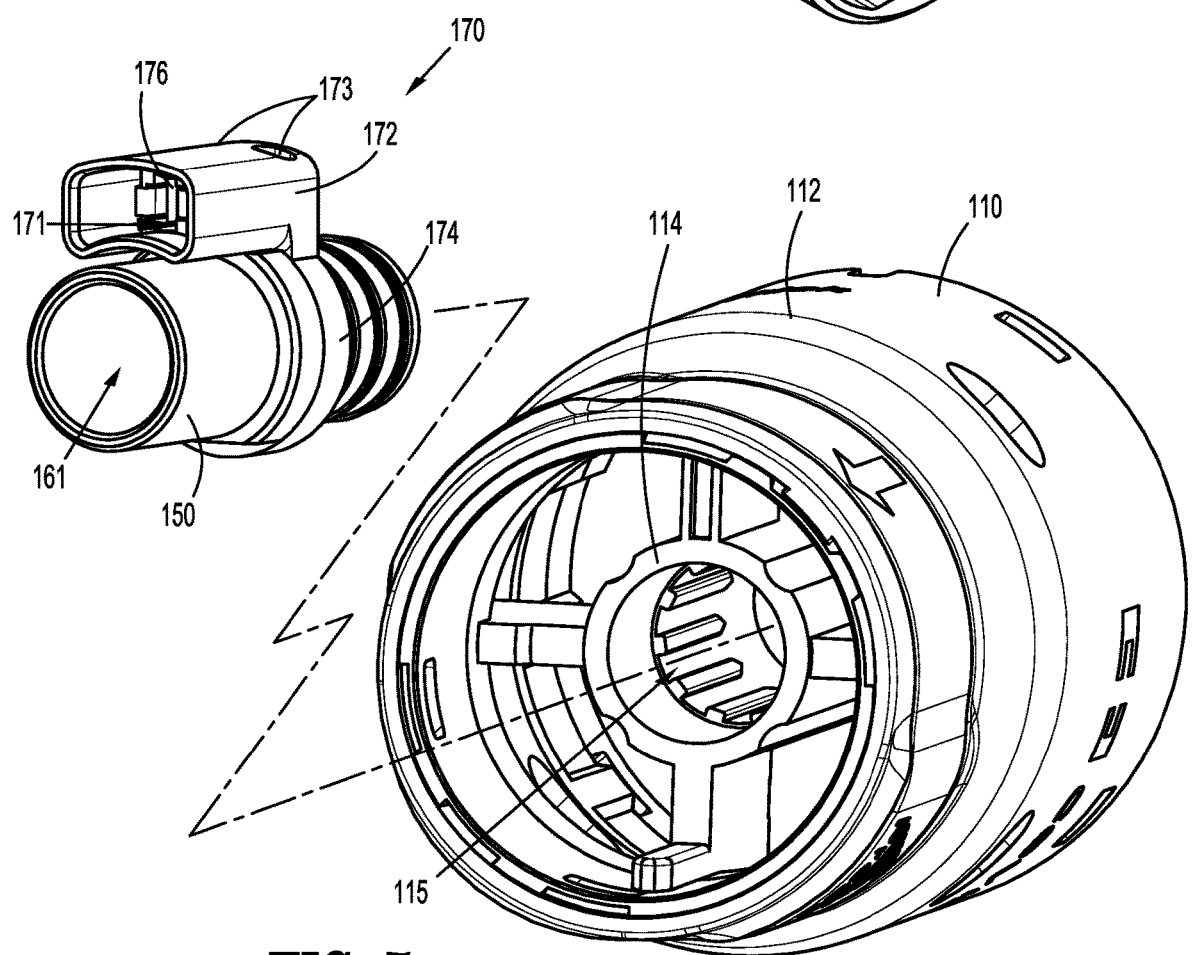
FIG. 5 is a perspective view from the distal end of the shell housing of the reload assembly shown in FIG. 2
Figure 6:
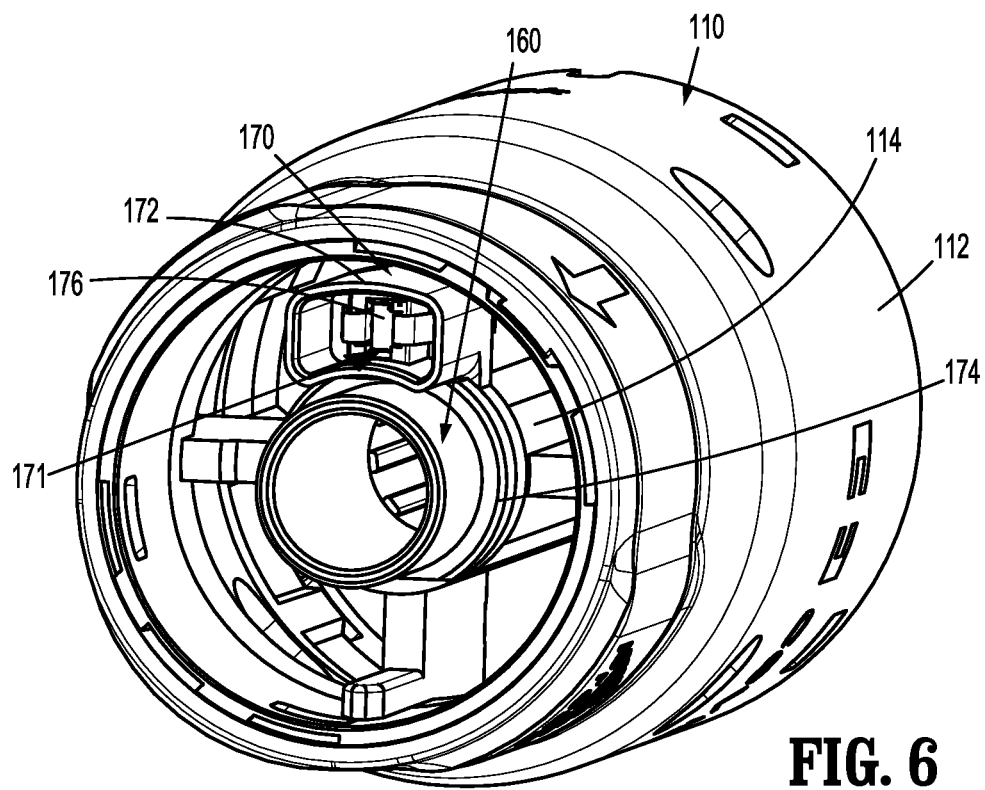
FIG. 6 is a perspective view from the distal end of the shell housing of the reload assembly shown in FIG. 2, including a bushing and a holder assembly separate from the reload assembly.

With reference to FIGS. 5 and 6, the inner housing portion 114 of the shell housing 110 defines a through bore 115 (FIG. 5) that receives an anvil shaft (not shown) of an anvil assembly 18 (FIG. 1). For a more detailed description of the anvil assembly, see, e.g., the '106 Patent. The through bore 115 receives a bushing 160 that defines a through bore 161 that is coaxial with the through bore 115. In embodiments, the bushing 160 is formed of a high strength material, e.g., metal, to provide added strength to the inner housing portion 114 of the shell housing 110.

Figure 7:
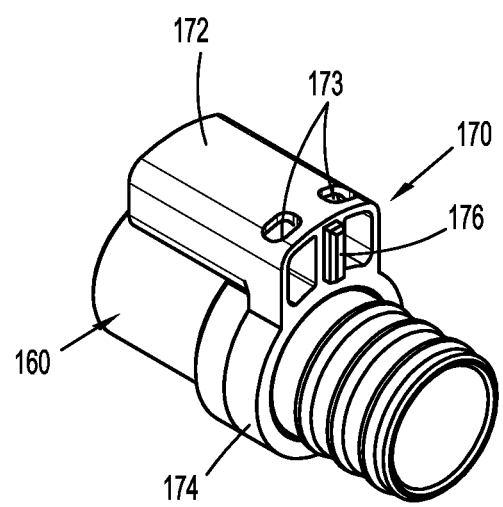
FIG. 7 is a perspective view from the distal end of the shell housing and staple cartridge of the reload assembly shown in FIG. 2 with the bushing and holder assembly received within the reload assembly.

With additional reference to FIG. 7, the reload assembly 100 includes an e-prom holder 170 that is received on the bushing 160 and supported within the shell housing 110. The e-prom holder 170 includes a housing portion 172 and an annular flange portion 174 extending from the housing portion 172. The housing portion 172 defines a cavity 171 (FIG. 5) for receiving an e-prom chip 176. As is known in the art, an e-prom chip communicates with the adaptor assembly 14 (FIG. 1) to provide information to the adaptor assembly 14 and the handle assembly 12 related to characteristics of the reload assembly 10. As will be described in further detail below, the housing portion 172 further defines a pair of openings 173 for receiving the hook portions 146 (FIG. 8) of the flexible arms 144 of the knife carrier 142. The annular flange portion 174 of the e-prom holder 170 is configured to be received about the bushing 160.

Figure 8:
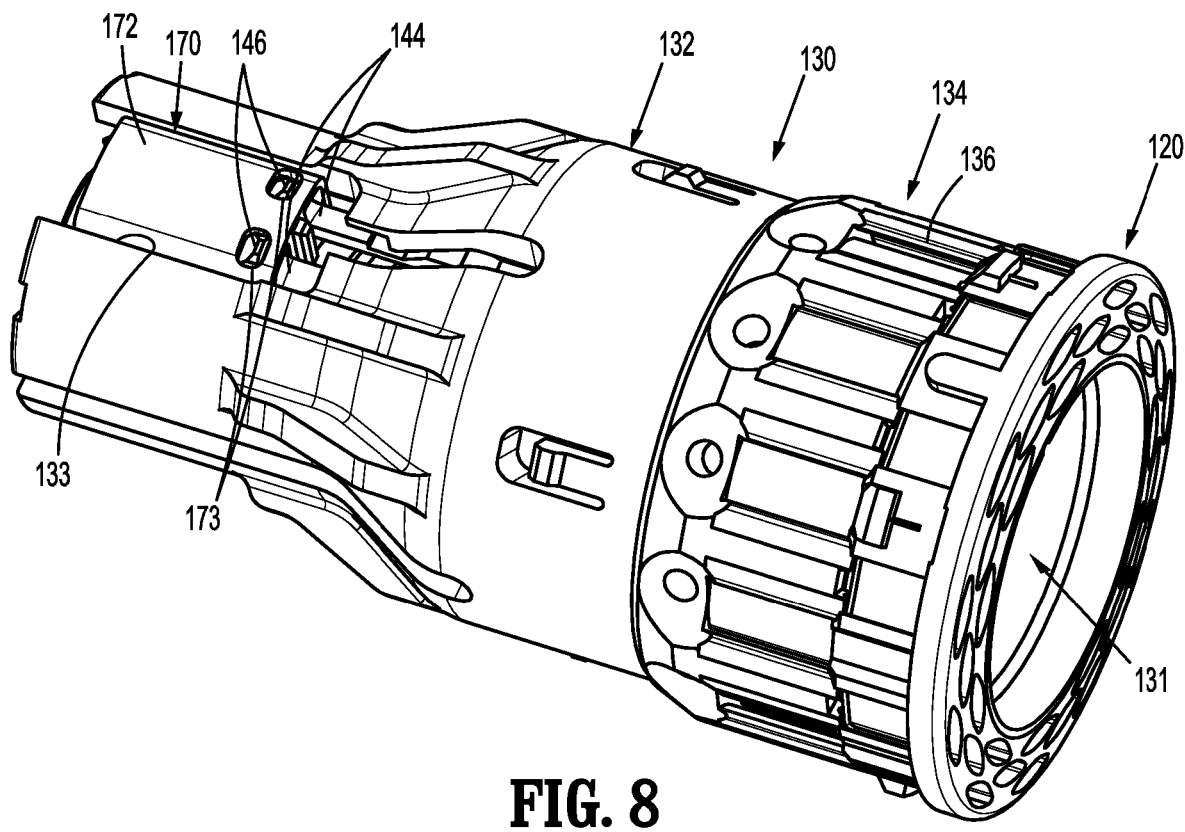
FIG. 8 is a perspective view of the reload assembly shown in FIG. 3 with the shell housing removed.
Figure 9:
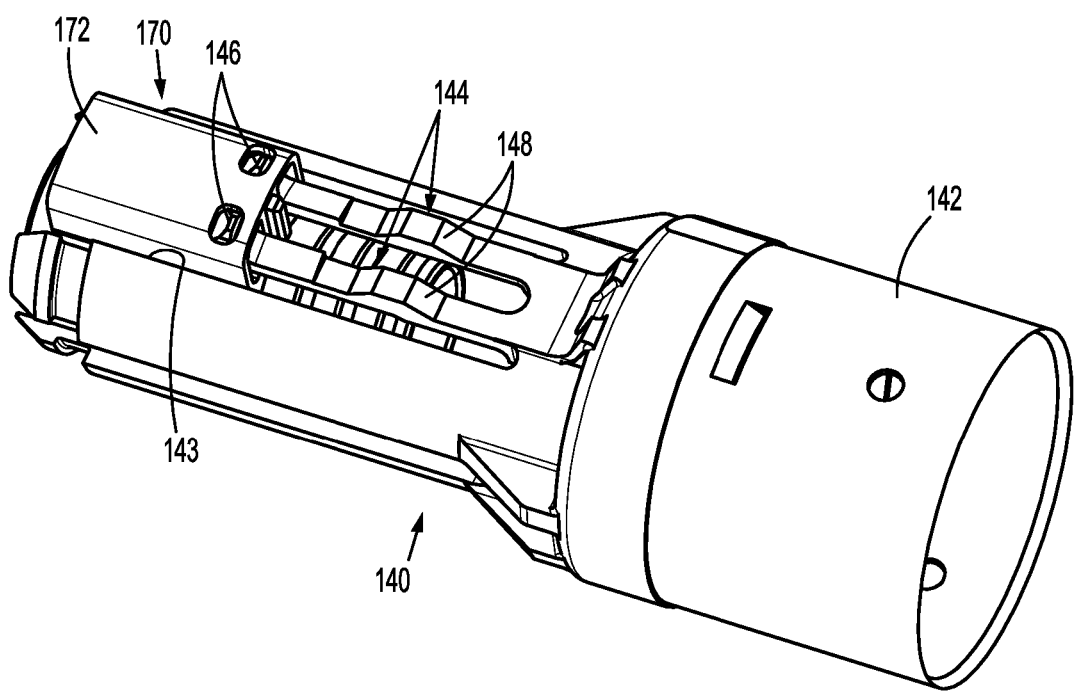
FIG. 9 is a perspective view of the reload assembly shown in FIG. 4 with the staple pusher assembly removed is a cross-sectional view taken along section line 8-8 of FIG. 2 with the reload assembly in a pre-fired position.
Figure 10:
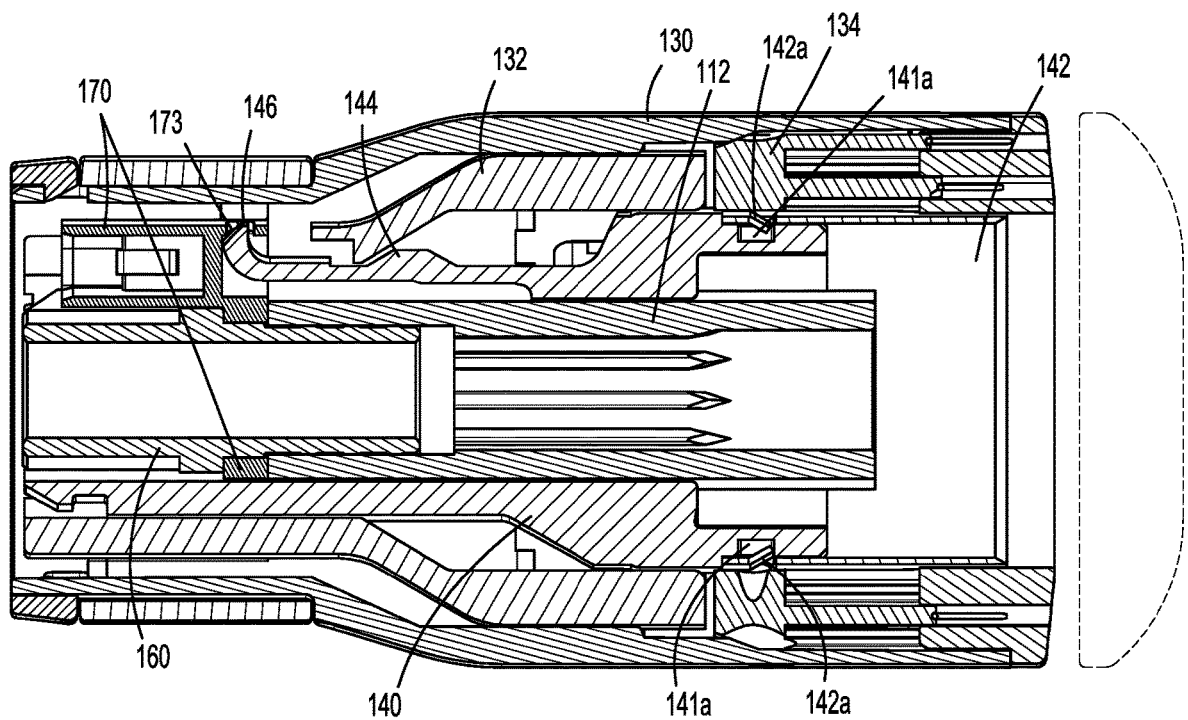
FIG. 10 is a cross-sectional view taken along section line 10-10 of FIG. 2 with the reload assembly in a pre-fired position.

Referring to FIGS. 8-10, each of the staple pusher member 132 of the pusher assembly 130 and the knife carrier 140 define a cutout 133 (FIG. 8), 143 (FIG. 9), respectively, that accommodates the e-prom holder 170 when the respective pusher assembly 130 and knife carrier 140 are in their retracted positions (FIG. 10).

With particular reference to FIG. 10, when the pusher assembly 130 and the knife carrier 140 are in their retracted positions, the hook portion 146 of the flexible arms 144 of the knife carrier 140 are received within the openings 173 in the housing portion 172 of the e-prom holder 170. Engagement of the hook portions 146 of the flexible arms 144 with the housing portion 172 of the e-prom holder 170 maintains the knife carrier 140 in its retracted position.

Figure 11:
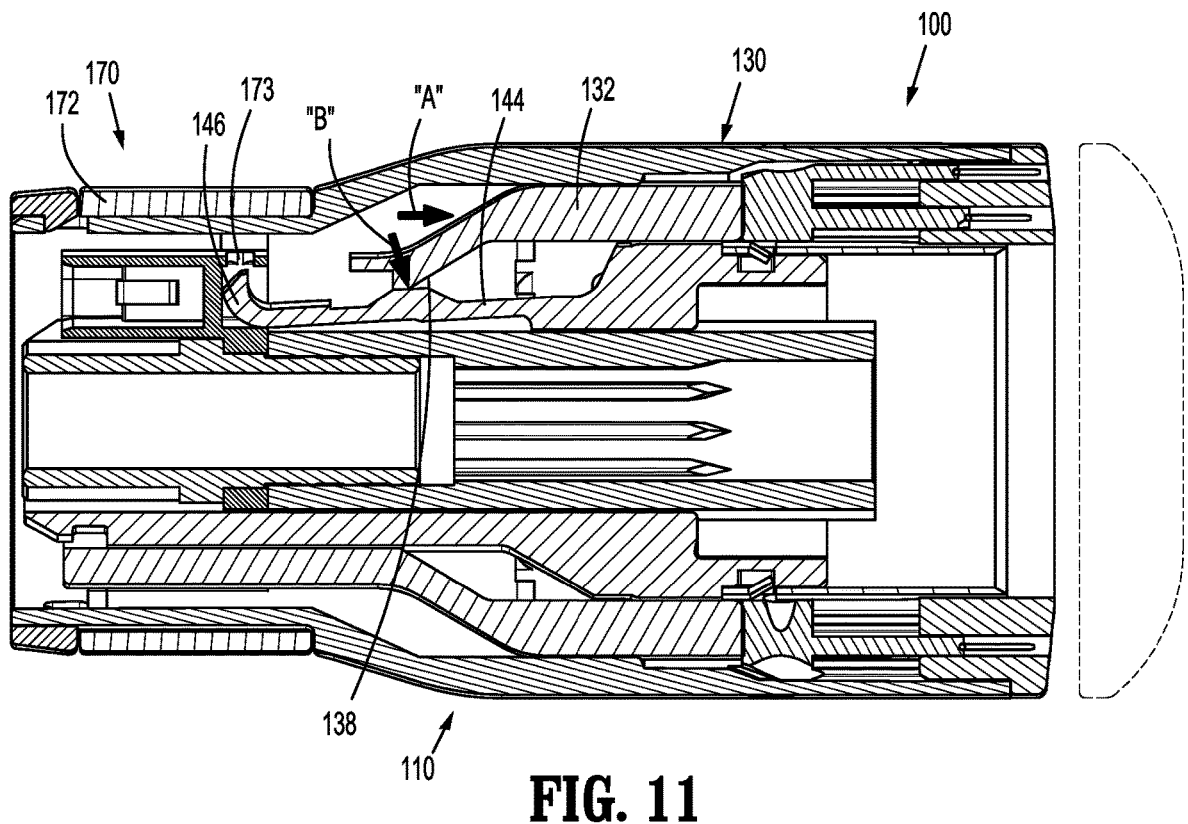
FIG. 11 is a cross-sectional view taken along section line 11-11 of shown in FIG. 10 with the pusher assembly of the reload assembly in a partially advanced position.

Turning to FIG. 11, the staple pusher member 132 of the pusher assembly 130 includes a tapered inner surface 138 that engages a ramped outer surface 148 on the flexible arms 144 of the knife carrier 140 as the staple pusher member 132 is moved distally a first distance within the shell housing 110, as indicated by arrow "A", to a partially advanced position. Engagement of the ramped outer surface 148 of the flexible arms 144 of the knife carrier 140 by the tapered inner surface 138 of the staple pusher member 132 of the pusher assembly 130 as the staple pusher member 132 moves distally causes the flexible arms 144 to flex radially inward, as indicated by arrow "B". Inward flexing of the flexible arms 144 retracts the hook portions 146 of the flexible arms 144 from within the openings 173 in the housing portion 172 of the e-prom holder 170 and out of engagement with the housing portion 172.

Figure 12:
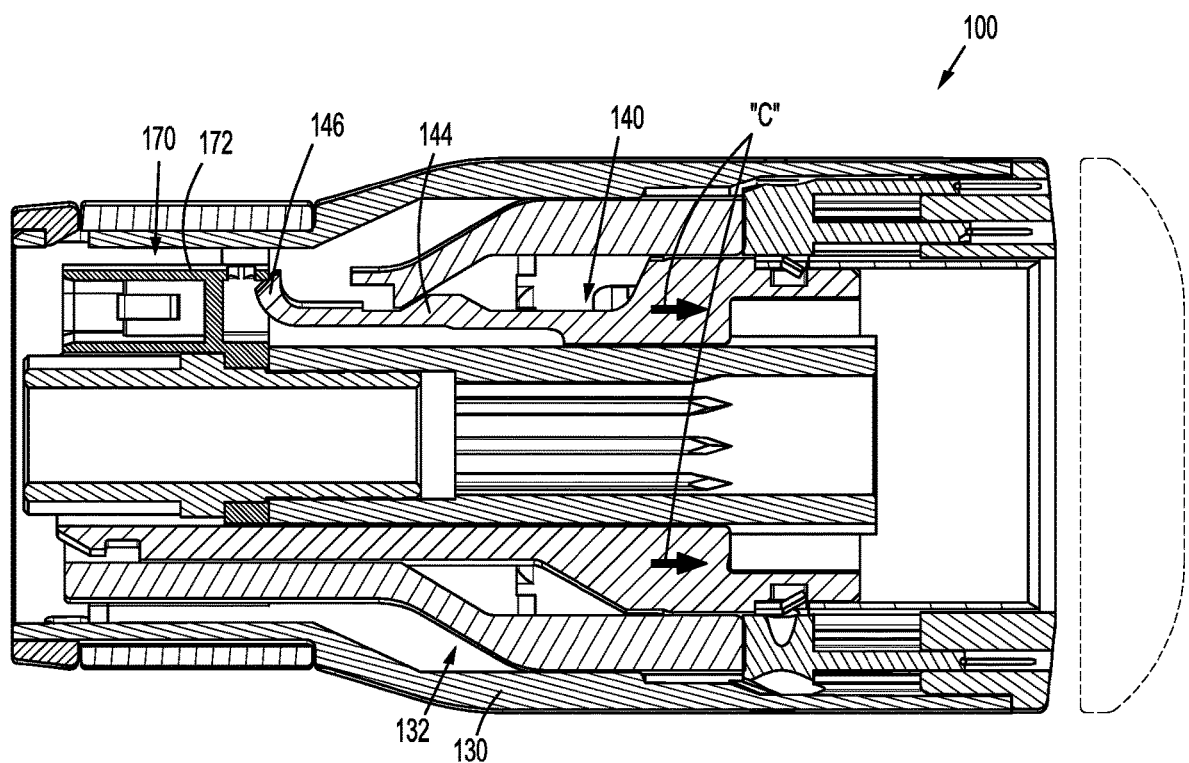
FIG. 12 is a cross-sectional view as shown in FIG. 10 with the knife carrier of the reload assembly in a partially advanced position.

Referring to FIG. 12, with the flexible arms 144 of the knife carrier 140 no longer engaged with the e-prom holder 170, the knife carrier 140 is advanced a second distance, as indicated by arrows "C", to a partially advanced position, to withdraw the hook portions 146 of the flexible arms 144 from within the housing portion 172 of the e-prom holder 170.

Figure 13:
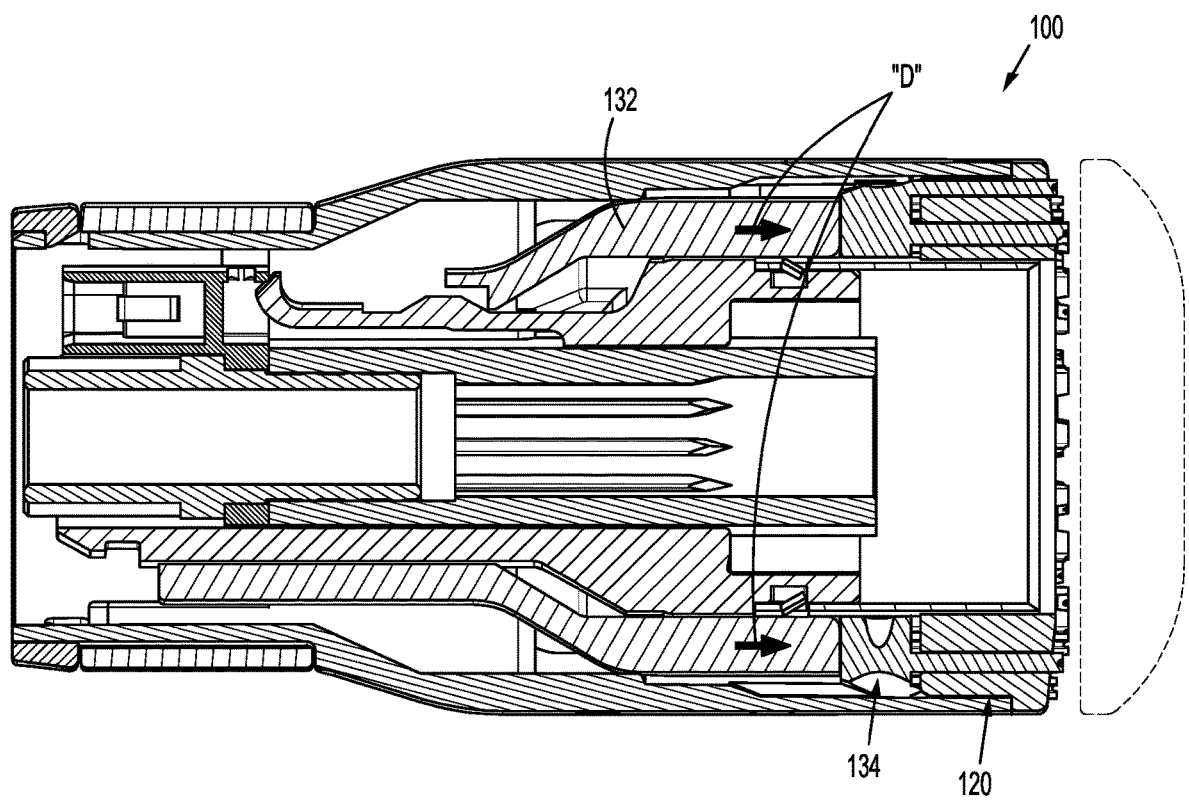
FIG. 13 is a cross-sectional view as shown in FIG. 10 with the pusher assembly in a fully advanced position.

Turning to FIG. 13, the staple pusher member 132 of the pusher assembly 130 is then advanced a third distance, as indicated by arrows "D", to a fully advanced position, to cause the advancement of annular pusher 134 of the pusher assembly 130 and the ejection of staples "S" (FIG. 3) from within the staple cartridge 120. Although shown as being a multistep process of moving the pusher assembly 130 a first distance to free the knife carrier 140 and then a second distance to eject the staples "S" from the staple cartridge 120, it is envisioned that the staple pusher member 132 may be configured to free the knife carrier 140 and eject staples "S" simultaneously or within the same stroke.

Referring to FIG. 14, either following or simultaneously with the second advancement of the pusher assembly 130, the knife carrier 140 is advanced a fourth distance, as indicated by arrows "E", to move of the annular knife 144 to a fully advanced position and cause the cutting of tissue (not shown) received between the staple cartridge 120 and the head assembly 18a of the anvil assembly 18.

Figure 15:
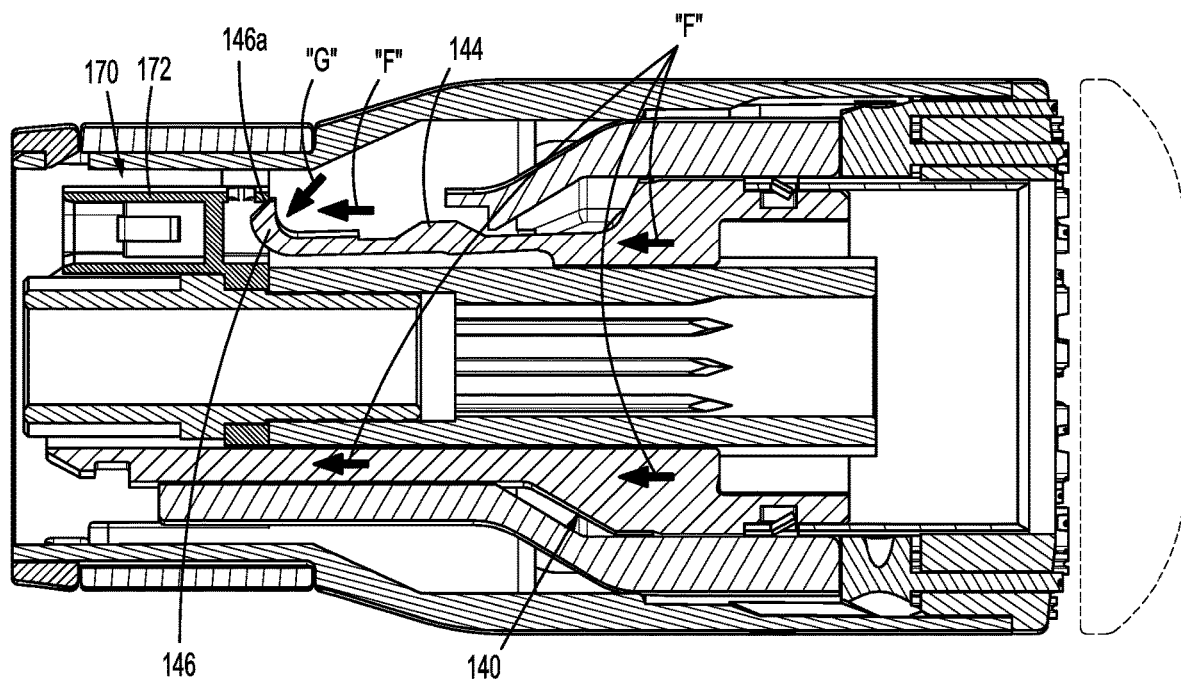
FIG. 15 is a cross-sectional view as shown in FIG. 10 with the knife carrier in a partially retracted position.

Turning to FIG. 15, following the cutting procedure, the knife carrier 140 is retracted, as indicated by arrows "F". As the knife carrier 140 is retracted, an angled surface 146a of the hook portion 146 of the flexible arms 144 of the knife carrier 140 engages the housing portion 172 of the e-prom holder 170 to cause inward flexing of the flexible arms 144, as indicated by arrow "G".

Figure 16:
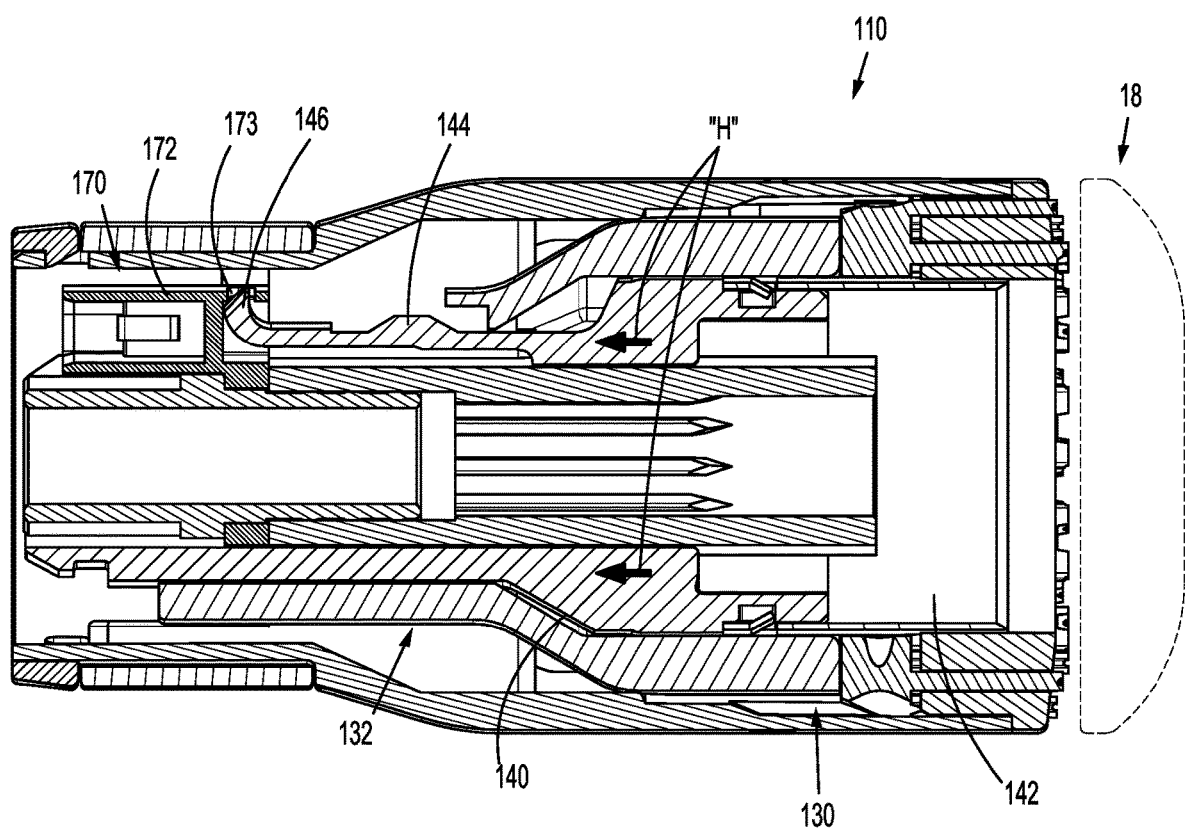
FIG. 16 is a cross-sectional view as shown in FIG. 10 with the knife carrier in a fully advanced positon.

As shown in FIG. 16, continued retraction of the knife carrier 140, as indicated by arrow "H", causes the hook portions 146 of the flexible arms 144 to be received within the openings 173 in the housing portion 172 of the e-prom holder 170 to reengage the flexible arms 144 of the knife carrier 140 with the housing portion 172 of the e-prom holder 170. Once the knife carrier 140 is reengaged with the e-prom holder 170, the knife carrier 140 and the annular knife 142 are prevented from subsequent advancement.

After the stapling procedure is completed, a clinician may want to remove a tissue donut from within the annular knife 142. When the clinician grasps the tissue donut and pulls the tissue donut distally to pull the tissue donut from the shell housing 110, engagement between the flexible arms 144 of the knife carrier and the housing portion 172 of the e-prom holder 170 prevents distal movement of the knife carrier 140 and the annular knife 142 to retain the annular knife 142 in a position recessed within the shell housing 110.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
    a shell housing including an inner housing portion and an outer housing portion, the inner housing portion spaced from the outer housing portion to define an annular cavity;
    a staple cartridge supported on a distal portion of the shell housing, the staple cartridge having a plurality of staple pockets, each of the staple pockets receiving a staple;
    a pusher supported within the annular cavity, the pusher movable from a retracted position, through a partially advanced position, to a fully advanced position;
    a knife carrier disposed within the annular cavity and defining a longitudinal axis, the knife carrier including at least one flexible arm having a free end, the at least one flexible arm having a hook portion on the free end; and
    a holder including a housing and a chip, the housing defining a cavity in which the chip is received and at least one opening for receiving the hook portion of the at least one flexible arm of the knife carrier, the hook portion of the at least one flexible arm being received within the at least one opening of the holder when the pusher is in the retracted position and being deflected from within the at least one opening when the pusher is in the partially advanced position.

2. The reload assembly of claim 1, wherein the pusher includes an inner tapered surface, and the at least one flexible arm includes a ramp portion, the inner tapered surface of the pusher engaging the ramp portion of the knife carrier when the pusher is in the partially advanced position.

3. The reload assembly of claim 1, further including a bushing secured to the inner housing portion, wherein the holder is secured to the bushing.

4. The reload assembly of claim 3, wherein the holder includes an annular flange portion receivable about the bushing.

5. The reload assembly of claim 1, wherein the at least one flexible arm includes two flexible arms.

6. The reload assembly of claim 1, wherein the hook portion includes an angled surface that engages the holder as the knife carrier moves from an advanced position to a retracted position.

7. The reload assembly of claim 1, wherein the knife carrier is moveable from a retracted position to an advanced position when the hook portion of the at least one flexible arm is spaced from the at least one opening in the holder.

8. The reload assembly of claim 1, wherein the knife carrier is secured to the holder when the hook portion of the at least one flexible arm is received within the at least one opening.

9. The reload assembly of claim 1, wherein the pusher includes an annular pusher and a pushing member, the pushing member including fingers that are received within the staple pockets of the staple cartridge.

10. The reload assembly of claim 1, further including an annular knife secured to the knife carrier.

11. The reload assembly of claim 1, wherein the chip is an e-prom chip.

12. A surgical stapling device comprising:
    a handle assembly; and
    a reload assembly releasably securable to the handle assembly, the reload assembly comprising:
        a shell housing;
        a staple cartridge supported on a distal portion of the shell housing, the staple cartridge having a plurality of staple pockets, each of the staple pockets receiving a staple;
        a pusher supported within the shell housing, the pusher movable from a retracted position, through a partially advanced position, to a fully advanced position;
        a knife carrier defining a longitudinal axis and supporting a knife, the knife carrier including at least one flexible arm having a free end, the at least one flexible arm having a hook portion on the free end; and
        a holder including a housing and a chip, the housing defining a cavity in which the chip is received and at least one opening for receiving the hook portion of the at least one flexible arm of the knife carrier, the hook portion of the at least one flexible arm being received within the at least one opening of the holder when the pusher is in the retracted position and being deflected from within the at least one opening when the pusher is in the partially advanced position.

13. The surgical stapling device of claim 12, wherein the pusher includes an inner tapered surface, and the at least one flexible arm includes a ramp portion, the inner tapered surface of the pusher engaging the ramp portion of the knife carrier when the pusher is in the partially advanced position.

14. The surgical stapling device of claim 12, wherein when the pusher is in the retracted position, the hook portion of the at least one flexible arm is received within the at least one opening of the holder.

15. The surgical stapling device of claim 12, further including a bushing secured within the shell housing, wherein the holder is secured to the bushing.

16. The surgical stapling device of claim 15, wherein the holder includes an annular flange portion receivable about the bushing.

17. The surgical stapling device of claim 12, wherein the hook portion includes an angled surface that engages the holder as the knife carrier moves from an advanced position to a retracted position.

18. The surgical stapling device of claim 12, wherein the knife carrier is moveable from a retracted position to an advanced position when the hook portion of the at least one flexible arm is spaced from the at least one opening in the holder.

19. The surgical stapling device of claim 12, wherein the knife carrier is secured to the holder when the hook portion of the at least one flexible arm is received within the at least one opening.

* * * * *